United States Patent [19]

Skotnicki et al.

[11] Patent Number: 5,216,162
[45] Date of Patent: Jun. 1, 1993

[54] SUBSTITUTED PYRROLO[3,2-C]QUINOLINES

[75] Inventors: Jerauld S. Skotnicki, Allentown; Robert M. Kearney, Lawrenceville, both of N.J.

[73] Assignee: American Home Products Corporation, New York, N.Y.

[21] Appl. No.: 936,825

[22] Filed: Aug. 28, 1992

[51] Int. Cl.⁵ .................. C07D 471/04; C07D 471/06
[52] U.S. Cl. ...................................................... 546/84
[58] Field of Search .......................................... 546/84

[56] References Cited

U.S. PATENT DOCUMENTS 3,887,566  6/1975  Rodway et al. ............... 546/84

OTHER PUBLICATIONS

Schonafinger et al. J. Het. Chem., vol. 25(2) 1988, pp. 535-537.

Primary Examiner—C. Warren Ivy
Assistant Examiner—P. G. Spivack
Attorney, Agent, or Firm—George Tarnowski

[57] ABSTRACT

There are disclosed compounds of the formula

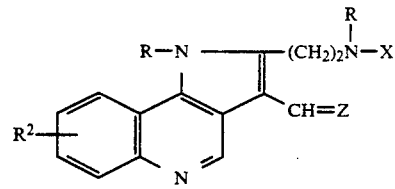

wherein
X is $R^1$,

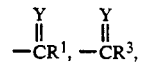

$-SO_2R^1$ or $-SO_2R^3$;
R is hydrogen or lower alkyl;
$R^1$ is unsubstituted or substituted pyridyl, indolyl or quinolinyl; or substituted phenyl, thienyl, furyl, benzothienyl or benzofuryl, where the foregoing substituted moieties are substituted with halo, lower alkylcarbonyl, benzoyl, carboxy, lower alkoxycarbonyl, $CON(R)_2$, $SO_2R^3$, cyano or trifluoromethyl;
$R^2$ is hydrogen, lower alkyl, phenyl, halo, lower alkoxy, hydroxy or trifluoromethyl;
$R^3$ is lower alkyl or phenyl;
Z is $-O-$, $-NNHR^4$, $-NNHR^1$, $-NOR^4$, $-NOR^1$, $-NOCH_2R^1$,

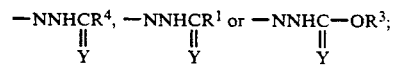

Y is O or S;
$R^4$ is hydrogen, lower alkyl or phenyl;
which by virtue of their ability to inhibit interleukin 1, are of use as antiinflammatory agents and in treatment of disease states involving enzymatic tissue destruction.

7 Claims, No Drawings

SUBSTITUTED PYRROLO[3,2-C]QUINOLINES

This invention relates to novel compounds possessing interleukin 1 (IL-1) antagonist activity and having antiinflammatory activity.

Interleukin 1 (IL-1) is a peptide hormone exhibiting a number of immune and inflammatory actions [Dinarello, *Rev. Inf. Dis.* 6, 51 (1984)]. IL-1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL-1 was originally shown to augment the proliferation of T lymphocytes for which it was named lymphocyte activating factor (LAF), and is believed to be important for the generation of T cell-dependent immune responses.

There is evidence to suggest a relationship between IL-1 and pathology in various diseases, particularly immunoinflammatory disorders such as rheumatoid arthritis [Dinarello et al., *Ann. Rev. Med.* 37, 173 (1986)]. IL-1 induces acute inflammatory responses producing soft tissue swelling (edema and erythema)[Granstein et al., *J. Clin. Invest.*, 77, 1010 (1986)]. It is a chemoattractant for polymorphonuclear leukocytes (PMN) and induces the activation and migration of these cells into tissues. IL-1 also stimulates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL-1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite et al., *J. Exp. Med.*, 157, 801 (1983)]. Furthermore, IL-1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL-1 mediates acute phase reactions including alterations in plasma divalent cations, increased synthesis by liver cells of acute phase proteins (C-reactive protein, serum amyloid A, etc.) and fever. Accordingly, compounds which have IL-1 antagonist activity and thereby inhibit the biological effects of IL-1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory/proliferative skin disorders as well as diseases in which the secretion of collagenase (and other tissue hydrolyzing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain novel substituted pyrrolo[3,2-c]quinolines antagonize the activity if IL-1, and so are useful as antiinflammatory agents and in the treatment of pathologies whose etiology is collagenase-based tissue destruction. The present invention provides novel compounds having the formula:

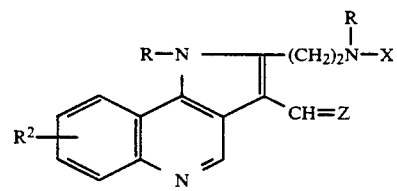

wherein
X is $R^1$,

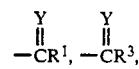

$-SO_2R^1$ or $-SO_2R^3$;

R is hydrogen or lower alkyl;

$R^1$ is unsubstituted or substituted pyridyl, indolyl or quinolinyl; or substituted phenyl, thienyl, furyl, benzothienyl or benzofuryl, where the foregoing substituted moieties are substituted with halo, lower alkylcarbonyl, benzoyl, carboxy, lower alkoxycarbonyl, $CON(R)_2$, $SO_2R^3$, cyano or trifluoromethyl;

$R^2$ is hydrogen, lower alkyl, phenyl, halo, lower alkoxy, hydroxy or trifluoromethyl;

$R^3$ is lower alkyl or phenyl;

Z is $-O-$, $-NNHR^4$, $-NNHR^1$, $-NOR^4$, $-NOR^1$, $-NOCH_2R^1$, $-NNHCR^4$, $-NNHCR^1$ or $-NNHC-OR^3$; and
$\phantom{-NNHCR^4,}\|\phantom{NNHCR^1}\|\phantom{NNHC-OR^3}\|$
$\phantom{-NNHCR^4,}Y\phantom{-NNHCR^1\,}Y\phantom{-NNHC-OR^3}Y$ Y is O or S;

$R^4$ is hydrogen, lower alkyl or phenyl.

The terms "lower alkyl" and "lower alkoxy" refer to moieties having 1 to 6 carbon atoms in the carbon chain.

The compounds of the invention can be prepared by the reaction of a tetrahydro-7H-pyrido[3',4':4,5]pyrrolo[3,2-c]quinoline with a suitable halo-$R^1$ reactant, and the reaction of the resultant compound with a suitable ZH reactant to yield final product.

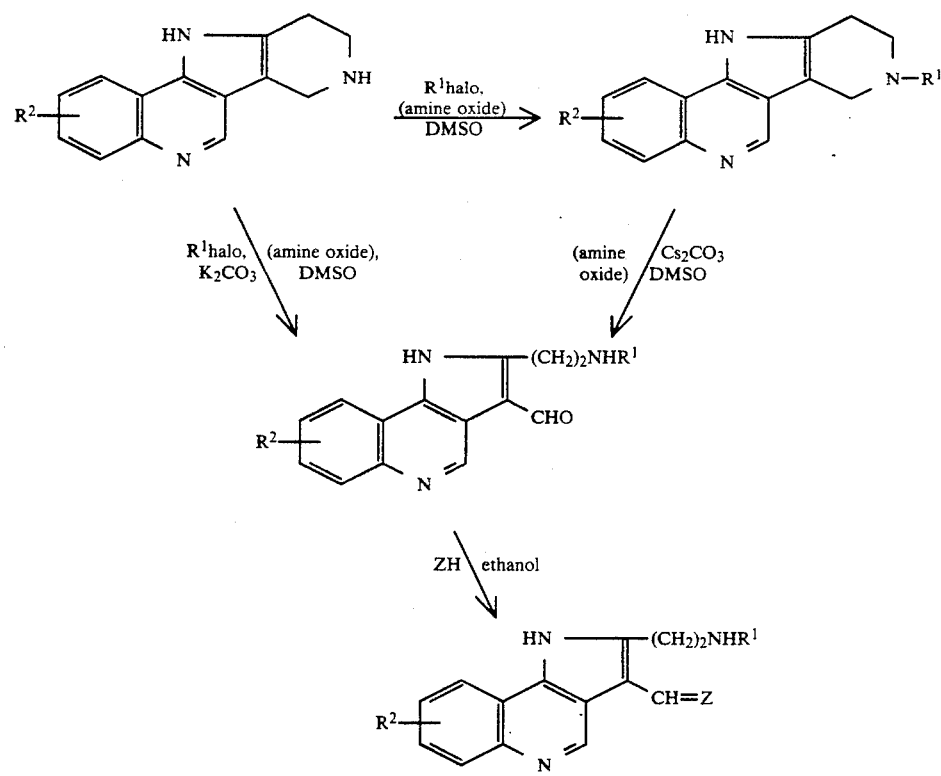

In the above reaction scheme, $R^1$, $R^2$ and Z are as defined hereinbefore. The compound 3-chloro-8,9.10,11-tetrahydro-7H-pyrido[3',4':4,5]pyrrolo[3,2-c]quinoline, which can be used as the starting material in the above scheme, is reported in *Journal of Heterocyclic Chemistry*, 25, 535 (1989). All other starting materials are commercially available or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the compounds of the invention are employed as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The interleukin 1 antagonist activity, as well as the antiinflammatory effects of the compounds of the invention may be demonstrated by standard pharmacological procedures, which are described more fully in the examples given hereinafter.

These procedures illustrate the ability of the compounds of the invention to inhibit the IL-1 -induced release of neutral protease from articular chondrocytes.

The following examples show the preparation and pharmacological testing of compounds within the invention.

EXAMPLE 1

4-[[2-(7-Chloro-3-formyl-1H-pyrrolo[3,2-c]-quinolin-2-yl)ethyl]amino]benzonitrile

A solution of 1.00 g (3.88 mmol) of 3-chloro-8,9,10,11-tetrahydro-7H-pyrido[3',4':4,5]pyrrolo[3,2-c]quinoline prepared according to the method reported in *J. Heterocyclic Chemistry*, 25, 535 (1988), 0.47 g (3.88 mmol) of p-fluorobenzonitrile, 0.54 g (3.88 mmol) of $K_2CO_3$ and 8 ml of dimethyl sulfoxide is stirred at 80° C. for 3 days. The reaction mixture is allowed to cool and is diluted with water producing a brown precipitate which is collected by filtration and dried. The crude product is purified by flash column chromatography (5% methanol in chloroform) to yield 0.06 g (4%) of the title compound as a yellow solid: m.p. 203°–206° C.; IR (KBr) 3380, 3200, 2200, 1650, 1600 cm$^{-1}$; NMR (DMSO-d$_6$) δ13.1 (s, 1H), 10.1 (s, 1H), 9.5 (s, 1H), 8.4 (d, 1H), 8.1 (d, 1H), 7.8–7.7 (m, 1H), 7.4 (d, 2H), 6.9 (t, 1H), 6.7 (d, 2H), 3.6 (q, 2H), 3.4 (t, 2H); m/e 375 (M+H).

Analysis for: $C_{21}H_{15}ClN_4O.\frac{1}{4}H_2O$. Calculated: C, 65.70; H, 4.46; N, 14.60. Found: C, 65.59; H, 4.01; N, 14.38.

EXAMPLE 2

4-[[2-(7-Chloro-3-formyl-1H-pyrrolo[3,2-c]quinolin-2-yl)ethyl]amino]benzoic acid ethyl ester

The title compound is prepared by the same reaction procedure as for the compound of Example 1 using 0.65 g (3.88 mmol) of ethyl-4-fluorobenzoate. A similar workup followed by further purification by flash column chromatography (ethyl acetate) yields 0.06 g (4%) of the title compound as a yellow solid: m.p. 194°–197° C.; IR (KBr) 3360, 3260, 1650, 1600 cm$^{-1}$; NMR (DMSO-d$_6$) δ10.0 (s, 1H), 9.5 (s, 1H), 8.4 (d, 1H), 8.1 (s, 1H), 7.7–7.6 (m, 3H), 6.7 (t, 1H), 6.6 (d, 2H), 4.2 (q, 2H), 3.6 (q, 2H), 3.4 (t, 2H), 1.2 (t, 3H); m/e 422 (M+H).

Analysis for: $C_{23}H_{20}ClN_3O_3.1\ H_2O$. Calculated: C, 62.80; H, 5.04; N, 9.55. Found: C, 62.33: H, 4.34; N, 9.38.

EXAMPLE 3

7-Chloro-2-[2-[[4-(methylsulfonyl)phenyl]amino]ethyl]-1H-pyrrolo[3,2-c]quinoline-3-carboxaldehyde

Method 1:

A mixture of 1.5 g (5.8 mmol) of 3-chloro-8,9,10,11-tetrahydro-7H-pyrido[3',4':4,5]pyrrolo[3,2-c]quinoline, 1.01 g (5.8 mmol) of p-fluorophenylmethylsulfone, 0.68 g (5.8 mmol) of 4-methylmorpholine N-oxide, 3.78 g (11.6 mmol) of $Cs_2CO_3$ and 10 ml of dimethyl sulfoxide is stirred overnight at 80° C. The reaction mixture is allowed to cool and is diluted with water to yield a brown precipitate which is collected by filtration and dried. The crude product is purified by column chromatography (6% methanol in chloroform) followed by trituration in ether/chloroform/methanol to yield 0.144 g (6%) of the title compound as an off white solid: m.p. 219°–220° C.; IR (KBr) 3320, 3210, 1640, 1590, 1130 cm$^{-1}$; NMR (DMSO-d$_6$) δ13.1 (s, 1H), 10.1 (s, 1H), 9.5 (s, 1H), 8.4 (d, 1H), 8.1 (d, 1H), 7.7 (m, 1H), 7.6 (d, 2H), 6.9 (t, 1H), 6.7 (d, 2H), 3.6 (q, 2H), 3.4 (t, 2H), 3.0 (s, 3H); m/e 428 (M+H).

Analysis for: $C_{21}H_{18}ClN_3O_3S.\frac{1}{4}H_2O$. Calculated: C, 58.20; H, 4.30; N, 9.70. Found: C, 58.13; H, 4.36; N, 9.60.

Method 2:

A. 3-Chloro-8,9,10,11-tetrahydro-8-[4-(methylsulfonyl)phenyl]-7H-pyrido[3',4':4,5]pyrrolo[3,2-c]quinoline A mixture of 1.5 g (5.8 mmol) of 3-chloro-8,9,10,11-tetrahydro-7H-pyrido[3',4':4,5]pyrrolo[3,2-c]quinoline, 1.01 g (5.8 mmol) of p-fluorophenylmethylsulfone, 0.68 g (5.8 mmol) of 4-methylmorpholine N-oxide, 3.78 g (11.6 mmol) and 10 ml of dimethyl sulfoxide is stirred overnight at 80° C. The reaction mixture is allowed to cool and is diluted with water to yield a brown precipitate which is collected by filtration and dried. The crude product is purified by flash chromatography (6% methanol in chloroform) to yield 0.15 g (6%) of product as a tan solid: m.p. >250° C.

B. 7-Chloro-2-[2-[[4-(methylsulfonyl)phenyl]amino]ethyl]-1H-pyrrolo[3,2-c]quinoline-3-carboxaldehyde A mixture of 3.0 g (7.28 mmol) of the compound of step A, above, 4.74 g (14.6 mmol) of $Cs_2CO_3$, 1.62 g (14.6 mmol) of trimethylamine N-oxide and 24 ml of dimethyl sulfoxide is stirred at 120° C. for 4 days. The reaction mixture is cooled and diluted with 400 ml of water producing a brown precipitate which is collected by filtration. The crude product is dissolved in methanol, filtered and evaporated onto silica gel. The coated silica gel is then added to a column and eluted with 10% methanol in chloroform to yield 0.75 g (24%) of title compound as an off white solid.

EXAMPLE 4

4-[[2-[7-Chloro-3-[(phenylhydrazono)methyl]-1H-pyrrolo[3,2-c]quinolin-2-yl]ethyl]amino]benzonitrile

A mixture of 0.026 g (0.07 mmol) of the compound of Example 1, 0.02 g (1.81 mmol) of phenylhydrazine and 15 ml of ethanol is stirred overnight at 85° C. The reaction mixture is cooled and concentrated in vacuo to produce a yellow solid which is washed with water and ether to produce 0.025 g (77%) of the title compound: NMR (DMSO-d$_6$) δ12.6 (s, 1H), 10.0 (s, 1H), 9.7 (s, 1H), 8.4 (d, 1H), 8.2 (s, 1H), 8.1 (s, 1H), 7.7 (m, 1H), 7.5 (d, 2H), 7.2 (t, 2H), 7.1 (d, 2H), 6.9 (t, 1H), 6.8–6.7 (m, 3H), 3.5 (q, 2H), 3.2 (t, 2H); m/e 465 (M+H).

Analysis for: $C_{27}H_{21}ClN_6.\frac{1}{4}H_2O$. Calculated: C, 68.86; H, 4.64; N, 17.85. Found: C, 68.66; H, 4.36; N, 17.45.

EXAMPLE 5

4-[[2-[7-Chloro-3-[(phenylhydrazono)methyl]-1H-pyrrolo[3,2-c]quinolin-2-yl]ethyl]amino]benzoic acid ethyl ester

A mixture of 0.22 g (0.52 mmol) of the compound of Example 2, 0.056 g (0.52 mmol) of phenylhydrazine and 25 ml of ethanol is stirred overnight at reflux. The reaction mixture is cooled and the ethanol is removed in vacuo to produce a brown residue to which ethyl acetate and water are added. The aqueous layer is extracted with ethyl acetate. The combined organic phases are concentrated under reduced pressure to give a brown solid. The crude product is purified by flash chromatography (5% methanol in chloroform) to yield 0.060 g (23%) of the title compound as a yellow solid: m.p. 223°–224° C. dec.; IR (KBr) 3360, 3280, 1680, 1590 cm$^{-1}$; NMR (DMSO-d$_6$) δ12.6 (s, 1H), 10.0 (s, 1H), 9.7 (s, 1H), 8.4 (d, 1H), 8.2 (s, 1H), 8.1 (d, 1H), 7.7–7.6 (m, 3H), 7.2 (t, 2H), 7.1 (d, 2H), 6.8 (t, 1H), 6.7–6.6 (m, 3H), 4.2 (q, 2H), 3.5 (q, 2H), 3.2 (t, 2H), 1.3 (t, 3H); m/e 512 (M+H).

Analysis for: $C_{29}H_{26}ClN_5O_2 \cdot \frac{1}{2}H_2O$. Calculated: C, 66.85; H, 5.20; N, 13.44. Found: C, 66.69; H, 5.20; N, 13.32.

EXAMPLE 6

7-Chloro-2-[2-[[4-(methylsulfonyl)phenyl]amino]ethyl]-1H-pyrrolo[3,2-c]quinoline-3-carboxaldehyde phenylhydrazone A mixture of 0.085 g (0.20 mmol) of the compound of Example 3 0.021 g (0.20 mmol) of phenylhydrazine and 25 ml of ethanol is stirred at reflux overnight. The reaction mixture is cooled and the ethanol is removed in vacuo to produce a yellow residue which is dissolved in ethyl acetate. The organic layer is washed with water, dried over $MgSO_4$, filtered and concentrated under reduced pressure to produce a yellow solid which is recrystallized from methanol/ether to yield 0.070 g (68%) of the title compound as a tan solid: m.p. 185°–186° C.; IR (KBr) 3350, 3280, 1585, 1120 cm$^{-1}$; NMR (DMSO-d$_6$) δ12.6 (s, 1H), 10.0 (s, 1H), 9.7 (s, 1H), 8.4 (d, 1H), 8.2 (s, 1H), 8.1 (d, 1H), 7.7 (m, 1H), 7.6 (d, 2H), 7.2 (t, 2H), 7.1 (d, 2H), 6.9 (t, 1H), 6.8 (d, 2H), 6.7 (t, 1H), 3.6 (q, 2H), 3.2 (t, 2H), 3.0 (s, 3H); m/e 518 (M+H).

Analysis for: $C_{27}H_{24}ClN_5O_2S \cdot \frac{3}{4}H_2O$. Calculated: C, 60.48; H, 5.72; N, 12.70. Found: C, 60.87; H, 4.77; N, 12.42.

EXAMPLE 7

The ability of the compounds of the inventions to inhibit interleukin 1 is measured by the ability of the test compounds to inhibit the IL-1-induced release of neutral protease from rabbit articular chondrocytes.

This assay is carried out as follows:
Isolation of rabbit chondrocytes

Male New Zealand white rabbits are anesthetized with 50 mg/kg of ketamine (i.m.) and killed by an intracardiac injection of 3 mls of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 minutes at 37° C. in 0.05% hyaluronidase (Sigma H-3884), rinsed with HBSS and incubated with 0.2% trypsin (Sigma T-2395) for 10 minutes at 37° C. The slices are rinsed again and incubated for 10 minutes at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% $CO_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates ($2 \times 10^5$ cells/well) and incubated at 27° C. until confluent (usually 4–6 days).

Stimulation of chondrocytes and drug treatment

The confluent chondrocytes are rinsed twice with serum-free Ham's F-12 medium and 1 ml is added to each well. Fifty μl of purified human IL-1 (100 Units/ml; Genzyme Corporation, Boston, MA) is then added to stimulate these cells to secrete neutral protease. To measure drug effects, the cells are treated with test compound 10 minutes prior to addition of IL-1. The standard screening dose is 10 μM. Twenty-four hours after IL-1 stimulation, supernatant fluids are collected and assayed for neutral protease activity.

Neutral protease assay

The neutral protease activity of chondrocyte supernatant fluids is determined by their ability to degrade an insoluble protease substrate, azocoll (Sigma). Supernatants are treated for 10 minutes at room temperature with 350 μM p-aminophenylmurcuric acetate to activate the latent enzyme. Three hundred of μl of supernatant is then mixed with 500 μl of a 20 mg/ml suspension of azocoll and incubated at 37° C. for 18–24 hours with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

% Inhibition of Protease Secretion =

$$\frac{A_{520} \text{ Untreated Supernatant} - A_{520} \text{ Drug Treated Supernatant}}{A_{520} \text{ Untreated Supernatant}} (\times 100)$$

Where tested in this assay, the compounds of the invention gave the following results:

| Compound of Example No. | Dose (μM) | % Inhibition (I.S.D.) |
| --- | --- | --- |
| 1 | 10 | 21 |
| 2 | 10 | 50 |
| 3 | 10 | 28 |
| 4 | 10 | 52 |
| 5 | 10 | 54 |
| 6 | 10 | 80 (IC$_{50}$ = 2.9 μM) |
|   | 1 | 23 |
|   | 0.1 | 14 |

What is claimed is:
1. A compound having the formula

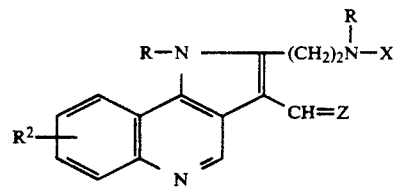

wherein
X is $R^1$,

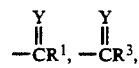

—SO$_2$R$^1$ or —SO$_2$R$^3$;
R is hydrogen or lower alkyl;
R$^1$ is unsubstituted or substituted pyridyl, indolyl or quinolinyl; or substituted phenyl, thienyl, furyl, benzothienyl or benzofuryl, where the foregoing substituted moieties are substituted with halo, lower alkylcarbonyl, benzoyl, carboxy, lower alkoxycarbonyl, CON(R)$_2$, SO$_2$R$^3$, cyano or trifluoromethyl;

R$^2$ is hydrogen, lower alkyl, phenyl, halo, lower alkoxy, hydroxy or trifluoromethyl;

R$^3$ is lower alkyl or phenyl;

Z is —O—, —NNHR$^4$, —NNHR$^1$, —NOR$^4$, —NOR$^1$, —NOCH$_2$R$^1$,

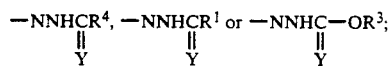

Y is O or S;

R$^4$ is hydrogen, lower alkyl or phenyl.

2. The compound of claim 1, having the name 4-[[2-(7-chloro-3-formyl-1H-pyrrolo[3,2-c]quinolin-2-yl)ethyl]amino]benzonitrile.

3. The compound of claim 1, having the name 4-[[2-(7-chloro-3-formyl-1H-pyrrolo[3,2-c]quinolin-2-yl)ethyl]amino]benzoic acid ethyl ester.

4. The compound of claim 1, having the name 7-chloro-2-[2-[[4-(methylsulfonyl)phenyl]amino]ethyl]-1H-pyrrolo[3,2-c]quinoline-3-carboxaldehyde.

5. The compound of claim 1, having the name 4-[[2-[7-chloro-3-[(phenylhydrazono)methyl]-1H-pyrrolo[3,2-c]quinolin-2-yl]ethyl]amino]benzonitrile.

6. The compound of claim 1, having the name 4-[[2-[7-chloro-3-[(phenylhydrazono)methyl]-1H-pyrrolo[3,2-c]quinolin-2-yl]ethyl]amino]benzoic acid ethyl ester.

7. The compound of claim 1, having the name 7-chloro-2-[2-[[4-(methylsulfonyl)phenyl]amino]ethyl]-1H-pyrrolo[3,2-c]quinoline-3-carboxaldehyde phenylhydrazone.

* * * * *